US008890076B2

(12) United States Patent
Dirksen et al.

(10) Patent No.: US 8,890,076 B2
(45) Date of Patent: Nov. 18, 2014

(54) BOLOMETER AND METHOD OF MANUFACTURING THE SAME

(71) Applicants: Peter Dirksen, Valkenswaard (NL); Sjoerd Hesdahl, The Hague (NL)

(72) Inventors: Peter Dirksen, Valkenswaard (NL); Sjoerd Hesdahl, The Hague (NL)

(73) Assignee: Koninklijke Philips N.V., Eindhoven (NL)

( * ) Notice: Subject to any disclaimer, the term of this patent is extended or adjusted under 35 U.S.C. 154(b) by 71 days.

(21) Appl. No.: 13/633,475

(22) Filed: Oct. 2, 2012

(65) Prior Publication Data

US 2013/0082182 A1 Apr. 4, 2013

Related U.S. Application Data

(60) Provisional application No. 61/542,423, filed on Oct. 3, 2011.

(51) Int. Cl.
*G01J 5/20* (2006.01)
*G01J 5/28* (2006.01)
*G01J 5/02* (2006.01)
*G01J 1/42* (2006.01)
*A61B 1/05* (2006.01)

(52) U.S. Cl.
CPC .. *G01J 5/28* (2013.01); *G01J 5/024* (2013.01); *G01J 5/20* (2013.01); *G01J 5/0225* (2013.01); *G01J 1/42* (2013.01); *A61B 1/05* (2013.01)
USPC ........................................................ 250/349

(58) Field of Classification Search
CPC ........................................................ G01J 5/20
USPC ........................................................ 250/349
See application file for complete search history.

(56) References Cited

U.S. PATENT DOCUMENTS

| 3,109,097 A * | 10/1963 | De Waard et al. ............ 250/352 |
| 6,262,417 B1 | 7/2001 | Ju |
| 2004/0166606 A1 * | 8/2004 | Forehand ...................... 438/106 |
| 2006/0116585 A1 | 6/2006 | Nguyen-Dinh et al. |

(Continued)

FOREIGN PATENT DOCUMENTS

| WO | 0164277 A2 | 9/2001 |
| WO | 2010137528 A1 | 12/2010 |

OTHER PUBLICATIONS

Zhuang et al.; "Two-Dimensional Capacitive Micromachined Ultrasonic Transducer (CMUT) Arrays for a Miniature Integrated Volumetric Ultrasonic Imaging System" Medical Imaging 2005: Ultrasonic Imaging and Signal Processing, Edited by William F. Walker, Stanislav Y. Emelianov, Proc. of SPIE vol. 5750 (SPIE, Bellingham, WA, 2005) pp. 37-46.

*Primary Examiner* — David Porta
*Assistant Examiner* — Hugh H Maupin

(57) ABSTRACT

The present invention relates to a bolometer (10) comprising a substrate (12), a first membrane (16) formed by removing a first sacrificial layer (14) on the substrate (12), the first membrane (16) comprising a measuring element (18) for measuring an amount of incident electromagnetic radiation (R), a second membrane (22) formed by removing a second sacrificial layer (20) on the first membrane (16), the second membrane (22) enclosing the first membrane (16), a first cavity (24) formed between the substrate (12) and the first membrane (16), and a second cavity (26) formed between the first membrane (16) and the second membrane (22). The present invention further relates to a method of manufacturing a bolometer, as well as a thermographic image sensor and medical device.

15 Claims, 10 Drawing Sheets

(56) References Cited

U.S. PATENT DOCUMENTS

| | | |
|---|---|---|
| 2011/0136284 A1 | 6/2011 | Huang |
| 2011/0151608 A1 | 6/2011 | Lemmerhirt et al. |
| 2011/0172543 A1 | 7/2011 | Hossack et al. |
| 2011/0241154 A1* | 10/2011 | Suzuki et al. ............ 257/467 |
| 2011/0266443 A1* | 11/2011 | Schimert et al. ......... 250/338.4 |

* cited by examiner

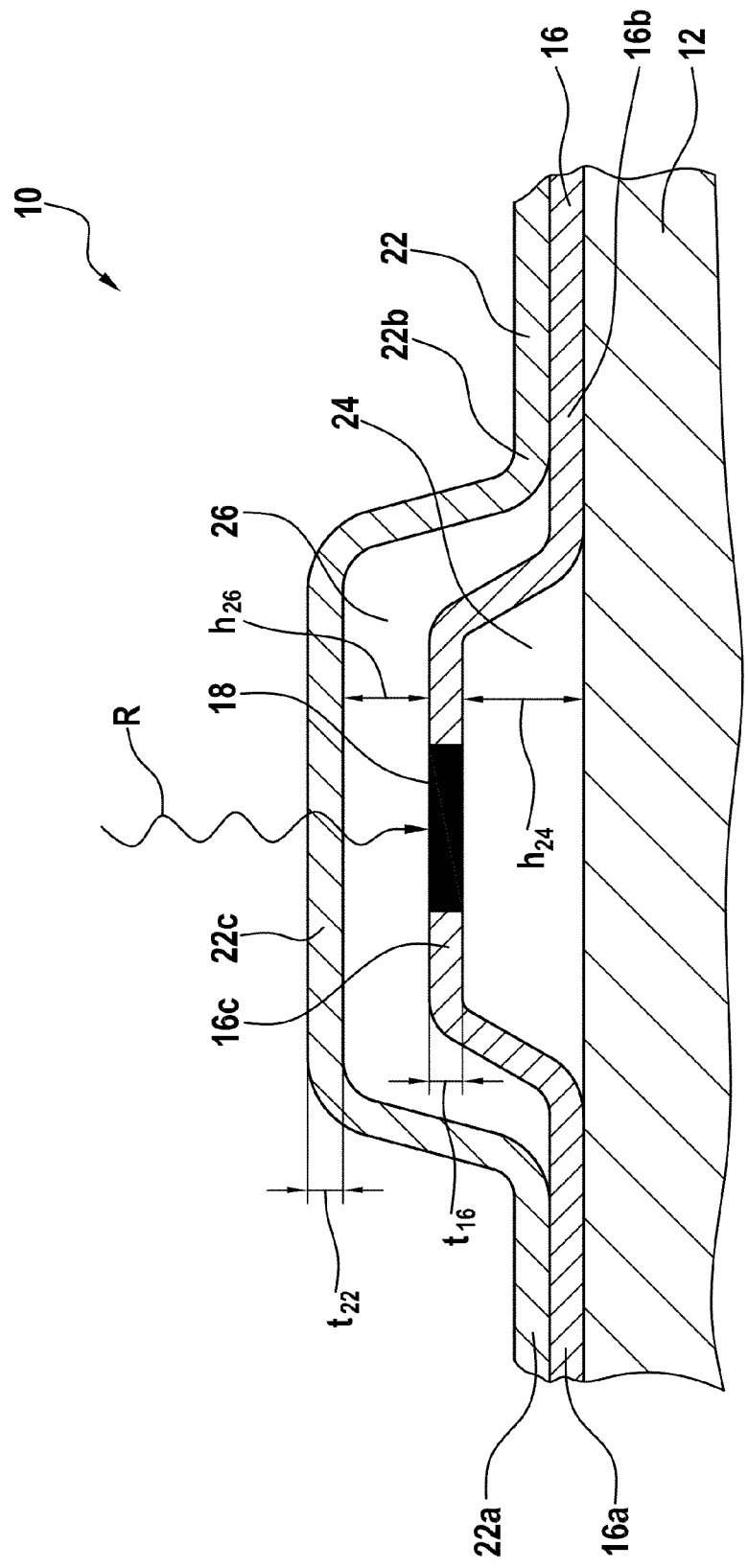

8,890,076 B2

BOLOMETER AND METHOD OF MANUFACTURING THE SAME

FIELD OF THE INVENTION

The present invention relates to a bolometer, in particular an infrared bolometer, and method of manufacturing the same. The present invention also relates to a thermographic image sensor for providing a thermographic image of an object irradiating electromagnetic radiation in form of infrared light, the thermographic image sensor comprising a plurality of such bolometers. The present invention also relates to a medical device comprising such thermographic image sensor.

BACKGROUND OF THE INVENTION

WO 01/64277 A2 discloses a device for the detection of vulnerable plaque within an artery. The device includes an elongate shaft having a distal end and a proximal end. A detector assembly is fixed to the elongate shaft proximate the distal end thereof. In one example, the detector assembly 726 includes a substrate 742 and a cover 744 that define a sensor array chamber 746. The cover 744 is sealingly fixed to substrate 742 by a bond 748. A plurality of pixels 751 are disposed on a top surface of substrate 742 of detector assembly 726 to obtain a thermal image of a strip of plaque and nearby vessel wall. Each pixel comprises a sensing element 752 and a cavity 750 defined by substrate 742.

Due to the sealingly fixation of the cover to the substrate by a bond, such detector assembly cannot be realized in small dimensions. Further, such bonding is not easy and expensive and in particular not suitable for mass manufacturing.

U.S. Pat. No. 6,262,417 B1 discloses an infrared bolometer including an active matrix level having a substrate and a pair of connecting terminals, a support level provided with a pair of bridges and a pair of conduction lines, an absorption level including a bolometer element surrounded by an absorber and a pair of posts positioned between the support level and the absorption level. Each of the bridges is provided with an anchor portion, a leg portion and an elevated portion, the anchor portion being affixed to the active matrix level and the elevated portion being apart from the active matrix level, wherein the elevated portion of each of the bridges including an inner part cantilevered from an outer part. Each of the posts includes an electrical conduit, wherein each ends of the bolometer element is electrically connected to the respective connecting terminal through the respective conduit and the respective conduction line.

A similar device is also disclosed in "Design and fabrication of a high fill-factor micro-bolometer using double sacrificial layers", Ju et al., SPIE Vol. 3698 Infrared Technology and Applications XXV (1999). The fabrication of this bolometer features that it uses double sacrificial layers so as to separate the absorber level from the bridge structure, electrical and thermal path between the absorber and substrate.

As the bolometric element is located in the upper membrane, such bolometer can suffer from a high thermal loss to the ambient air and/or can be fragile.

SUMMARY OF THE INVENTION

It is an object of the present invention to provide an improved, in particular with low thermal loss and/or robust, bolometer and method of manufacturing the same, as well as a corresponding thermographic image sensor and medical device.

In a first aspect of the present invention a bolometer is presented comprising a substrate, a first membrane formed by removing a first sacrificial layer on the substrate, the first membrane comprising a measuring element for measuring an amount of incident electromagnetic radiation, a second membrane formed by removing a second sacrificial layer on the first membrane, the second membrane enclosing the first membrane, a first cavity formed between the substrate and the first membrane, and a second cavity formed between the first membrane and the second membrane.

In a further aspect of the present invention a thermographic image sensor is presented for providing a thermographic image of an object irradiating electromagnetic radiation in form of infrared light, the thermographic image sensor comprising a plurality of such bolometers according to the invention which are arranged in an array on a common substrate.

In a further aspect of the present invention a medical device (e.g. endoscope or catheter) comprising such thermographic image sensor according to the invention is presented.

In a further aspect of the present invention a method of manufacturing a bolometer is presented, the method comprising the steps of providing a first sacrificial layer on a substrate, providing a first membrane on the first sacrificial layer, the first membrane comprising a measuring element for measuring an amount of absorbed incident electromagnetic radiation, providing a second sacrificial layer on the first membrane, providing a second membrane on the second sacrificial layer such that the second membrane encloses the first membrane, removing the first sacrificial layer such that a first cavity is formed between the substrate and the first membrane, and removing the second sacrificial layer such that a second cavity is formed between the first membrane and the second membrane.

It is a basic idea of the present invention to provide a double cavity bolometer (or also called double membrane structured bolometer). A second membrane is used to enclose (or encapsulate) a first membrane comprising the measuring element (or also called bolometric element). The second membrane acts as an optical aperture and protects the bolometer against influences of the environment. Further, the second membrane increases the thermal isolation of the bolometer significantly, in particular only if the second cavity is filled with a gas having a pressure lower than the atmospheric pressure (e.g. vacuum). The function of the first membrane comprising the measuring element is to mechanically support and thermally isolate the measuring element (e.g. thermistor) from its surroundings. The substrate functions as a heat sink. The first cavity also thermally isolates the measuring element. Such bolometer can in particular be manufactured using thin film deposition techniques. The two cavities are formed by removing sacrificial layers. As the cavities are filled with the sacrificial layers for most of the manufacturing process, the bolometer is very robust, thus contributing to a high yield. Further, the bolometer, manufacturing method and corresponding thermographic image sensor is highly miniaturized and/or suitable for mass manufacturing.

In a first embodiment, the first membrane comprises two end portions where the first membrane is attached to a planar surface of the substrate and a middle portion arranged on the first sacrificial layer such that the middle portion of the first membrane is spaced apart from the planar surface of the substrate when the first sacrificial layer is removed. In this way no holes need to be created in the substrate, but the first membrane and the first cavity can be formed by simply removing a sacrificial layer (using an etching step). Providing or applying the first membrane can in particular be performed using thin film deposition. This facilitates the manufacturing process and thus reduces costs.

In a further embodiment, the second membrane comprises two end portions where the second membrane is attached to the first membrane and a middle portion arranged on the second sacrificial layer such that the middle portion of the second membrane is spaced apart from the first membrane when the second sacrificial layer is removed. In this way the second membrane (enclosing the first membrane) and the second cavity can be easily formed by simply removing a sacrificial layer (using an etching step). Providing or applying the second membrane can in particular be performed using thin film deposition techniques. This facilitates the manufacturing process and thus reduces costs.

In a further embodiment, the incident electromagnetic radiation is infrared light. In this embodiment the bolometer is an infrared bolometer. The infrared light can in particular have a wavelength between 8 µm and 15 µm, in particular about 10 µm. This wavelength is particularly suitable to detect infrared light irradiated by an object, for example an object having a temperature between 15° C. and 45° C., in particular having a temperature around room temperature (e.g. 300K).

In a variant of this embodiment, the second membrane has a thickness which is selected such that the infrared light can pass through the second membrane to the measuring element. The thickness of the second membrane is thus well chosen and in particular small.

In a further embodiment, the bolometer further comprises a cover layer on the second membrane, and comprises a hole in the cover layer to provide a window where the incident electromagnetic radiation can pass through the second membrane to the measuring element. In this way the bolometer has a higher thickness at the edges of the bolometer than in the centre of the bolometer. In this way it is ensured that the electromagnetic radiation can pass through the second membrane in the window (or centre) of the bolometer, while by means of the cover layer a good mechanical support of the thin second membrane is provided (at the edges of the bolometer). Further, the cover layer ensure a reliable sealing (e.g. vacuum sealing) of the cavities.

In a variant of this embodiment, the cover layer is made of silicone nitride. Thus material is especially advantageous. For, example the cover layer made of silicone nitride can be provided or applied using plasma-enhanced chemical vapor deposition (PECVD). In a further embodiment, a total diameter of the bolometer is between 20 µm and 90 µm, in particular between 40 µm and 60 µm, in particular about 50 µm. In this way a very small bolometer can be provided.

In a further embodiment, the second membrane has a thickness between 0.3 µm and 0.8 µm, in particular between 0.4 µm and 0.6 µm. In particular the thickness can be about 0.5 µm. These thicknesses are sufficiently thin such that infrared light (in particular having a wavelength between 8 µm and 15 µm, in particular about 10 µm) can pass through the second membrane to the measuring element, and at the same time the second membrane can resist ambient air pressure (about 1 Bar), in dependence on the diameter or area of the bolometer (in particular for a total diameter of the bolometer of between 20 µm and 90 µm, in particular between 40 µm and 60 µm, in particular about 50 µm).

In a further embodiment, the first membrane comprises a single measuring element. In this way thermal coupling between two or multiple measuring elements can be prevented. Further, compared to a solution where multiple measuring elements are enclosed or covered by a one single membrane, the total diameter of the bolometer is smaller and thus the thickness of the enclosing or covering membrane can be thinner, while still withstanding ambient air pressure (about 1 Bar).

In a further embodiment, the substrate comprises a mirror layer comprising a reflective mirror for reflecting the incident electromagnetic radiation. This further improves the sensitivity of the bolometer.

In a further embodiment the first cavity has a height which is bigger than a height of the second cavity.

In a further embodiment, the first sacrificial layer and the second sacrificial layer are removed in a common etching step. This facilitates manufacturing of the bolometer and thus reduces costs. For example, an etching agent can be introduced through an etch hole in the second membrane. For example, the first cavity and the second cavity can be connected (e.g. through a hole in the first membrane) such that the sacrificial layers can be etched in a common etching step.

In a further embodiment, an etch hole is provided in the second membrane which is sealed with a seal or plug. In this way the sacrificial layer(s) can be easily etched and the cavities can be sealed. The etch hole and corresponding plug can in particular be provided at an edge of the bolometer (in a region where the first membrane is attached to the planar surface of the substrate). In combination with the cover layer, the cover layer can cover the seal or plug. This further improves the sealing of the cavities.

In a variant of this embodiment, also the first membrane comprises a hole. An etching agent, introduced through the etch hole in the second membrane, can reach to the first sacrificial layer through the hole in the first membrane. In this way both the first and second sacrificial layers can be easily etched in one common etching step.

In a further embodiment, the first cavity and/or the second cavity comprises a gas having a pressure lower than the atmospheric pressure. This increases the thermal isolation of the measuring element significantly. The gas can for example be (low-pressure) gas remainders that are accumulated in the first and/or second cavity during manufacturing (in particular during sealing with the seal or plug). For example, the gas can comprise at least one of $SiH_4$, $NH_3$, $N_2$, and reaction products. For example, the pressure of the gas can be between 0.5 and 5 Torr, in particular between 2 and 3 Torr, or vacuum.

In a further embodiment, the measuring element is embedded in or attached to a layer of the first membrane.

In a variant of this embodiment the first membrane comprises multiple layers. For example, the first membrane can comprises a lower layer, a middle layer on the lower layer, and a top player on the middle layer, the measuring element being embedded in the middle layer.

In a preferred embodiment, the measuring element is a thermistor (or also called temperature dependent resistor). In this way a high sensitivity and small measuring element can be provided. For example, the thermistor can be embedded in or attached to a layer of the first membrane. For example, the thermistor can be made of metal (e.g. a metal layer or metal element).

In a variant of this embodiment, interconnects are attached to the thermistor which connect the thermistor to an electrical circuit for sensing a resistance change of the thermistor. In this way a temperature change of the thermistor can be detected. For example, the interconnects can be embedded in or attached to a layer of the first membrane.

In a further embodiment, the membranes and layers are provided by thin film deposition.

Preferred embodiments of the invention are defined in the dependent claims, it shall be understood that the claimed method or thermographic image sensor has similar and/or identical preferred embodiments as the claimed bolometer and as defined in the dependent claims.

BRIEF DESCRIPTION OF THE DRAWINGS

These and other aspects of the invention will be apparent from and elucidated with reference to the embodiment(s) described hereinafter. In the following drawings FIG. 1 shows a schematic cross-section of a bolometer according to a first embodiment.

DETAILED DESCRIPTION OF THE INVENTION

Figure 2A:
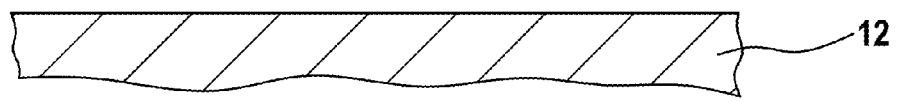
FIG. 2a-f show steps of a method of manufacturing the bolometer according to the first embodiment.

FIG. 1 shows a schematic cross-section of a (infrared) bolometer 10 according to a first embodiment. The bolometer 10 comprises a substrate 12. The bolometer 10 further comprises a first membrane 16 formed by removing a first sacrificial layer on the substrate 12. The first membrane 16 comprises a measuring element 18 for measuring an amount of incident (infrared) electromagnetic radiation R. In the shown embodiment the first membrane 16 comprises a single measuring element 18. The treasuring element 18 preferably is be a thermistor (or also called temperature dependent resistor). In this way a high sensitivity and small measuring element can be provided. The bolometer comprises interconnects (not shown) which are attached to the thermistor and which connect the thermistor to an electrical circuit for sensing a resistance change of the thermistor. In this way a temperature change of the thermistor can be detected. The resistance change of the thermistor is proportional to the temperature change. Alternatively, the measuring element can also be any other suitable measuring element for measuring the amount of incident (infrared) electromagnetic radiation, such as for example a thermopile.

The bolometer further comprises a second membrane 22 formed by removing a second sacrificial layer on the first membrane 16. The second membrane 22 encloses (or encapsulates) the first membrane 16. A first cavity 24 is formed between the substrate 12 and the first membrane 16, and a second cavity 26 is formed between the first membrane 16 and the second membrane 22. The first cavity 24 and/or the second cavity 26 comprise a gas having a pressure lower than the atmospheric pressure (e.g. vacuum).

In FIG. 1 the first membrane 16 comprises two end portions 16a, 16b where the first membrane 16 is attached to a planar surface of the substrate 12 and a middle portion 16c arranged on the first sacrificial layer such that the middle portion 16c of the first membrane 16 is spaced apart from the planar surface of the substrate 12 (by the cavity 24) when the first sacrificial layer is removed. The second membrane 22 comprises two end portions 22a, 22b where the second membrane 22 is attached to the first membrane 16 and a middle portion 22c arranged on the second sacrificial layer such that the middle portion 22c of the second membrane 22 is spaced apart from the first membrane 16 (by the cavity 26) when the second sacrificial layer is removed.

In the embodiment shown in FIG. 1, the incident electromagnetic radiation R is infrared light. The infrared light can in particular have a wavelength between 8 μm and 15 μm, in particular about 10 μm. The second membrane 22 has a thickness $t_{22}$ which is selected such that the infrared light can pass through the second membrane 22 to the measuring element 18. In this way a maximum allowable thickness can be defined. Further, the thickness can be selected to resist ambient air pressure (about 1 Bar), in dependence on the diameter or area of the bolometer. In this way a minimum allowable thickness can be defined. The thickness $t_{22}$ of the second membrane is thus well chosen and in particular small. The second membrane 22 can in particular be chosen such that the product of thickness and attenuation coefficient of the second membrane material is small (e.g. smaller than 1). As known from the Beer-Lambert law, the measured amount or intensity I of electromagnetic radiation (light) transmitted through a layer of material with thickness x is related to the incident intensity $I_0$ according to the inverse exponential power law $I=I_0 e^{-\alpha x}$, where x denotes the thickness of the layer (e.g. thickness $t_{22}$ of second membrane 22) and $\alpha$ is the attenuation coefficient (e.g. attenuation coefficient of the second membrane 22).

Taking these considerations into account, the second membrane 22 can in particular have a thickness $t_{22}$ between 0.3 μm and 0.8 μm, in particular between 0.4 μm and 0.6 μm, in particular about 0.5 μm. For these thicknesses it has shown that the infrared light (in particular between 8 μm and 15 μm, in particular about 10 μm) can pass through the second membrane 22. At the same time the second membrane 22 is thick enough to resist ambient air pressure.

The first membrane 16 can in particular have a thickness $t_{16}$ between 0.3 μm and 1.7 μm, in particular between 0.5 μm and 1.5 μm. Furthermore, the first cavity 24 can have a height $h_{24}$ which is bigger than a height $h_{26}$ of the second cavity 26, as shown in FIG. 1. The first cavity 24 can have a height $h_{24}$ which is between ⅛ and ½ of the wavelength of the electromagnetic radiation, in particular about ¼ of the wavelength (e.g. a height $h^{24}$ of 2.5 μm for a wavelength of 10 μm).

Figure 2B:
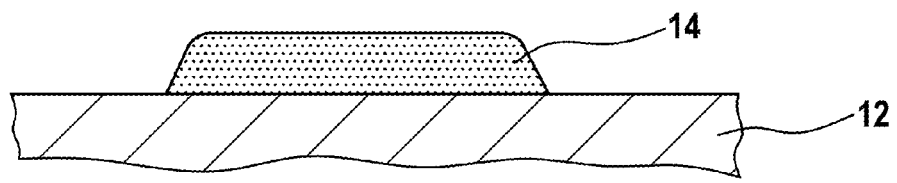
Figure 2C:
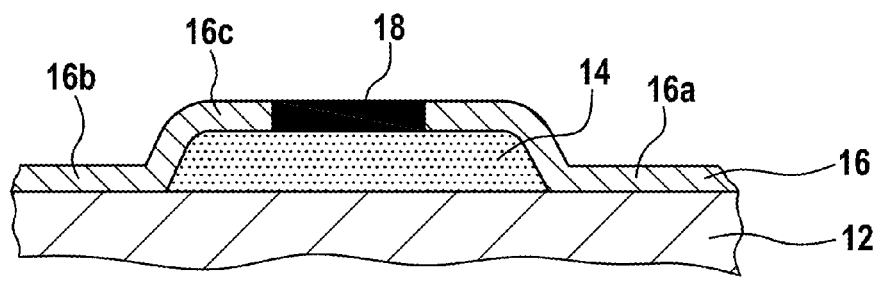
Figure 2D:
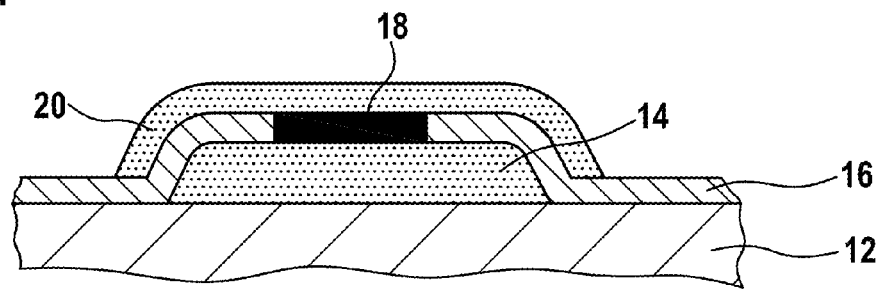
Figure 2E:
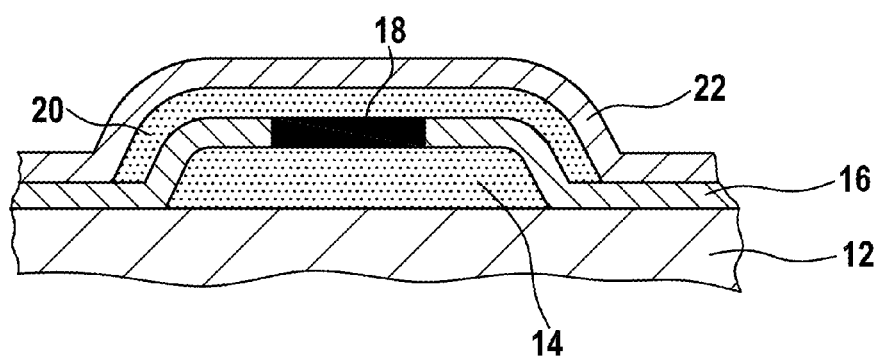
Figure 2F:
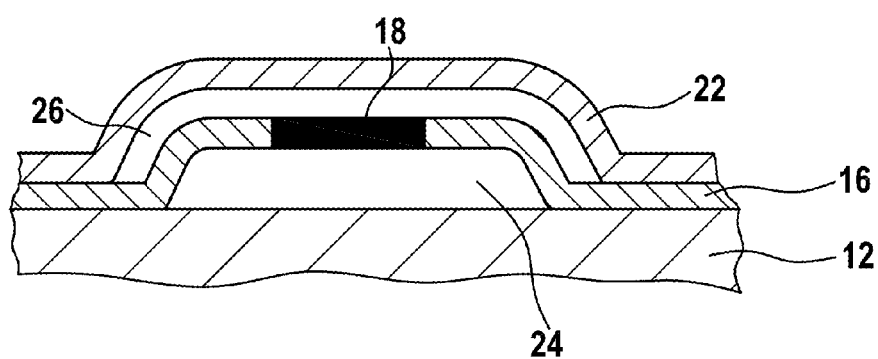

FIG. 2a-f show steps of a (thin film deposition) method of manufacturing the bolometer 10 according to the first embodiment, as shown in FIG. 1. After a substrate 12 is provided, as shown in FIG. 2a, a first sacrificial layer 14 is provided (or applied or deposited) on the substrate 12, as shown in FIG. 2b. Afterwards, a first membrane 16 is provided or applied or deposited) on the first sacrificial layer, as shown in FIG. 2c. The first membrane 16 comprises a measuring element 18 (in particular thermistor) for measuring an amount of absorbed incident electromagnetic radiation R. Then, a second sacrificial layer 20 is provided (or applied or deposited) on the first membrane 16, as shown in FIG. 2d. Subsequently, a second membrane 22 is provided (or applied or deposited) on the second sacrificial layer 20 such that the second membrane 22 encloses the first membrane 16, as shown in FIG. 2e. Afterwards, the first sacrificial layer is removed such that a first cavity 24 is formed between the substrate 12 and the first membrane 16, and the second sacrificial layer 20 is removed such that a second cavity 26 is formed between the first membrane 16 and the second membrane 22, as shown in FIG. 2f. The first sacrificial layer 14 and the second sacrificial layer 20 are removed in a common etching step. In this embodiment the membranes and layers described are provided by thin film deposition.

Figure 3:
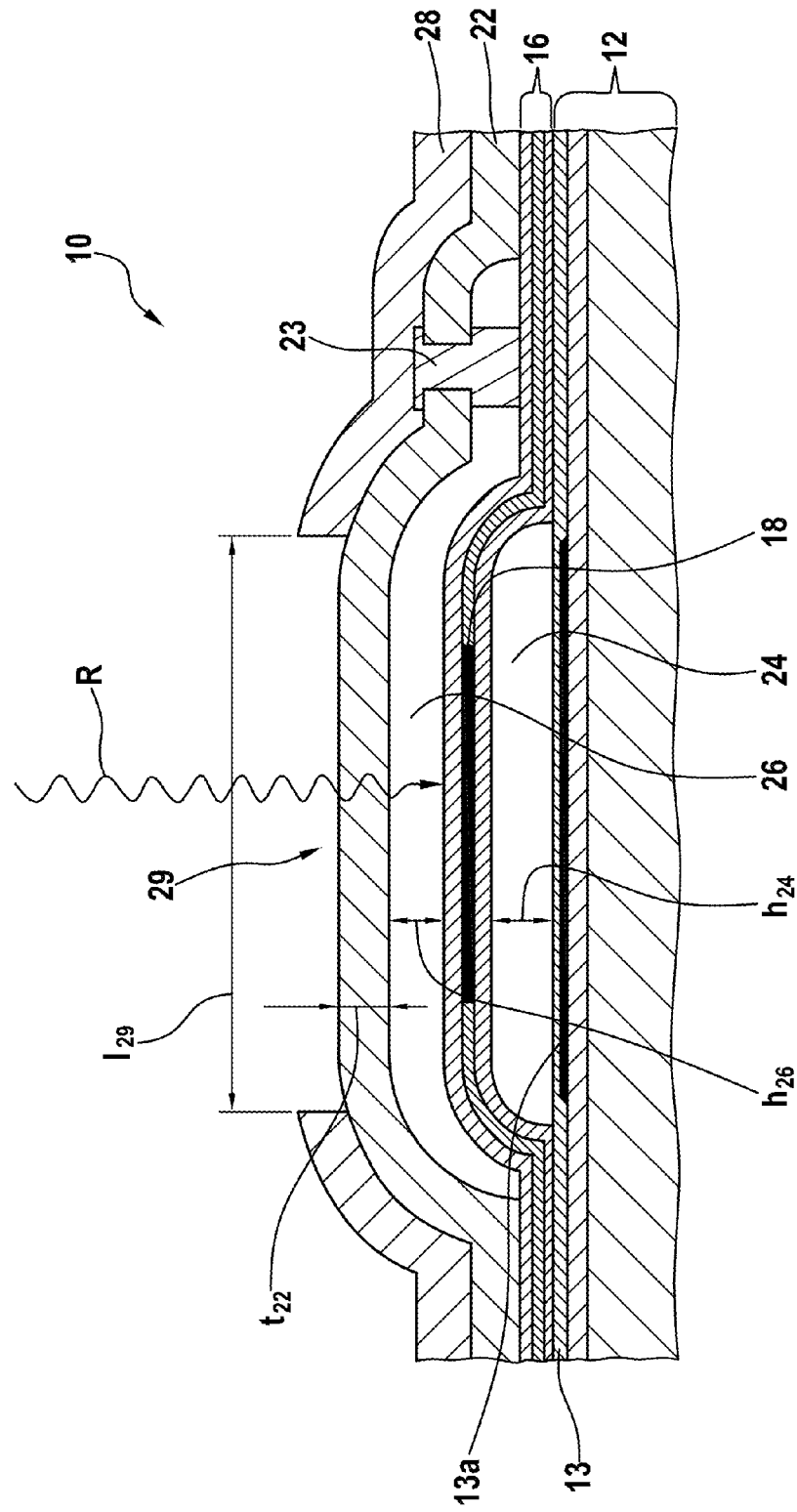
FIG. 3 shows a schematic cross-section of a bolometer according to a second embodiment.

FIG. 3 shows a schematic cross-section of a (infrared) bolometer according to a second embodiment, in particular a variant of the first embodiment of FIG. 1. The explanations made for the first embodiment with reference to FIG. 1 therefore also apply for the second embodiment. Compared to the first embodiment of FIG. 1, the bolometer 10 further comprises a cover layer 28 on the second membrane 22, and comprises a hole 29 in the cover layer 28 to provide a window where the incident electromagnetic radiation R can pass through the second membrane 22 to the measuring element 18. In this way the bolometer has a higher thickness at the edges of the bolometer than in the centre of the bolometer. The hole 29 has a length $l_{29}$. The length $l_{29}$ is bigger than a length of the measuring element (or thermistor) 18. As can be seen in FIG. 3, the measuring element 18 (or thermistor) is embedded in a layer of the first membrane 16. This is achieved by providing a first membrane 16 having multiple layers. As can be seen in FIG. 3, the first membrane 16 comprises a lower layer, a middle layer on the lower layer, and a top layer on the middle layer, the measuring element 18 being embedded in the middle layer. Further, compared to the first embodiment of FIG. 1, the substrate 12 comprises a mirror layer 13 comprising a reflective mirror 13a for reflecting the incident electromagnetic radiation R. Also, at the edge of the bolometer (in a region where the first membrane 16 is attached to the planar surface of the substrate 12 (end portion of first membrane)), an etch hole is provided in the second membrane 22 which is sealed with a seal or plug 23. Multiple etch holes and corresponding seals or plugs 23 can be provided at the edges of the bolometer. The cover layer 28 covers the seal(s) or plug(s) 23.

Figure 4A:
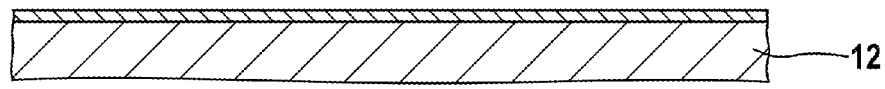
FIG. 4a-g show steps of a method of manufacturing the bolometer according to the second embodiment.
Figure 4B:
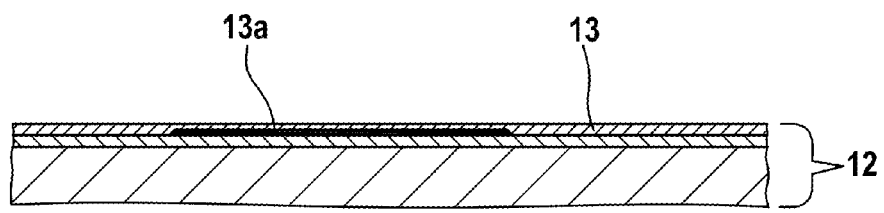
Figure 4C:
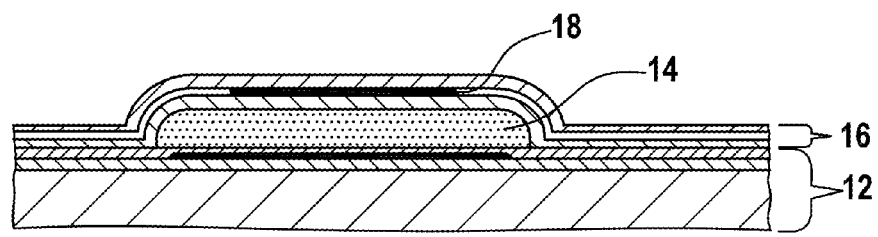
Figure 4D:
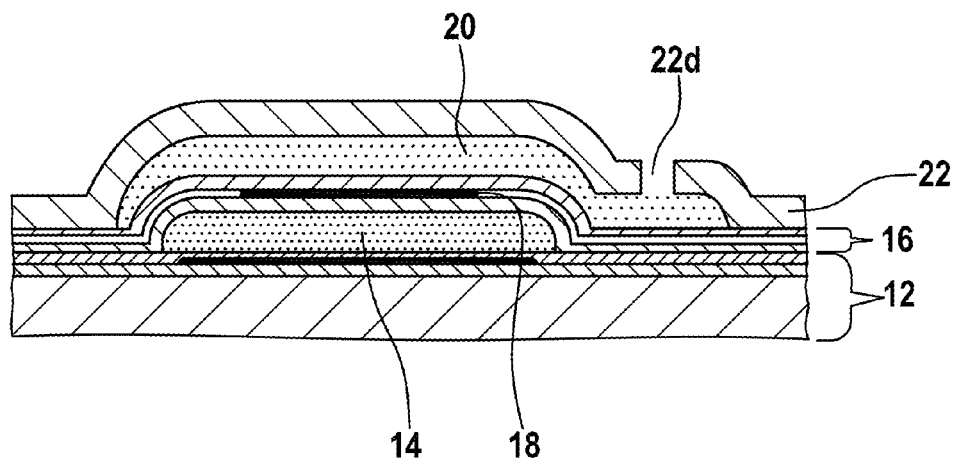
Figure 4E:
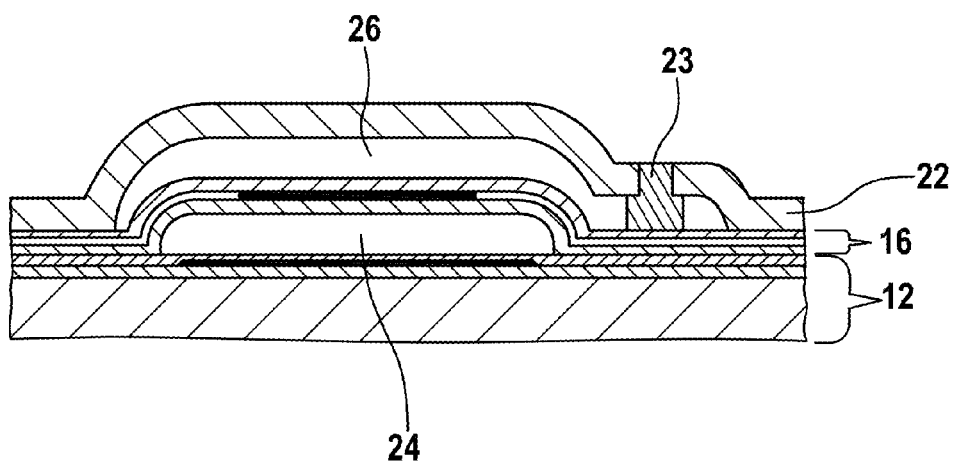
Figure 4F:
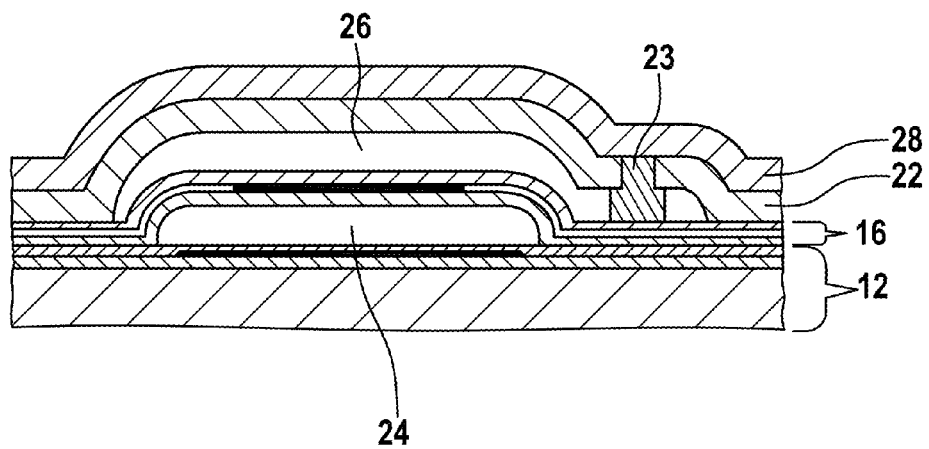
Figure 4G:
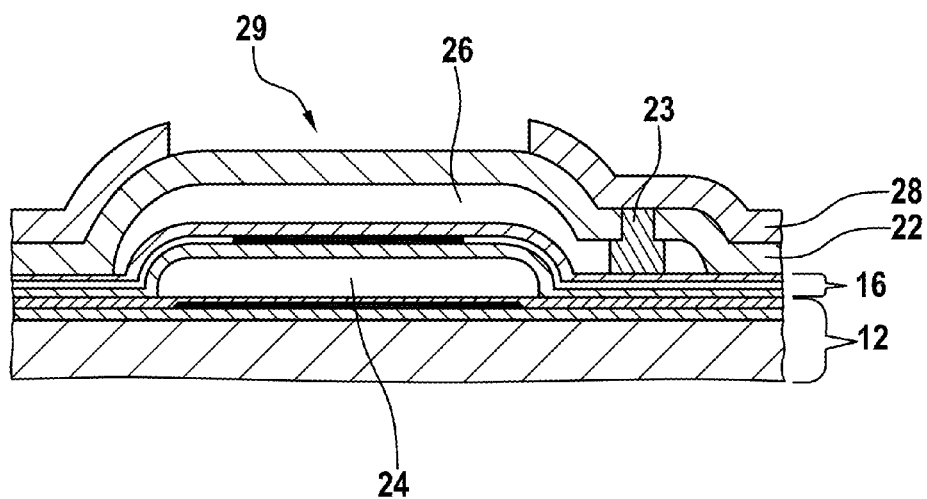

FIG. 4a-g show steps of a (thin film deposition) method of manufacturing the bolometer according to the second embodiment, as shown in FIG. 2. After a substrate 12 is provided, as shown in FIG. 4a, a mirror layer 13 is provided (or applied or deposited) on the substrate 12, as shown in FIG. 4b. For example, the substrate can be a wafer with a silicon oxide electrical isolation layer. The mirror layer 13 comprises a reflective mirror 13a for reflecting the incident electromagnetic radiation R. For example, the mirror layer 13 comprising the mirror 13a therein can be a silicone oxide layer. Afterwards, a first sacrificial layer 14 is provided (or applied or deposited) on the substrate 12 (shown in FIG. 4c), and then a first membrane 16 is provided on the first sacrificial layer 14 (also shown in FIG. 4c). The first membrane 16 comprises a measuring element 18 for measuring an amount of absorbed incident electromagnetic radiation R, as explained with reference to the first embodiment of FIG. 1 and FIG. 2. Then, a second sacrificial layer 20 is provided (or applied or deposited) on the first membrane 16 (shown in FIG. 4d), and subsequently a second membrane 22 is provided (or applied or deposited) on the second sacrificial layer 20 such that the second membrane 22 encloses the first membrane 16 (also shown in FIG. 4d). Then, an etch hole 22d is provided in the second membrane 22 (also shown in FIG. 4d). Afterwards, the first sacrificial layer is removed such that a first cavity 24 is formed between the substrate 12 and the first membrane 16, and the second sacrificial layer 20 is removed such that a second cavity 26 is formed between the first membrane 16 and the second membrane 22, as shown in FIG. 4e. The first sacrificial layer 14 and the second sacrificial layer 20 are removed in a common etching step by introducing an etching agent. The etching agent is introduced through the etch hole 22d. The first membrane 16 comprises a hole 16d (not shown) through which the etching agent, introduced through the etch hole 22d, reaches to the first sacrificial layer 14. After the first sacrificial layer 14 and the second sacrificial layer 20 have been etched (by the etching agent), the first cavity 24 and/or the second cavity 26 are provided with air having a pressure lower than the atmospheric pressure. Then, a seal or plug 23 is provided in the etch hole 22d to seal the etch hole 22d, as shown in FIG. 4e. For example, the seal or plug 23 can be provided by sputtering an aluminium layer in the etch hole 22d. Afterwards, a cover layer 28 is provided (or applied or deposited) on the second membrane as shown in FIG. 4f. For example, the cover layer 28 can be made of silicone nitride. Subsequently, a hole 29 is provided in the cover layer 28 by removing part of the cover layer 28, as shown in FIG. 4g. The hole 29 provides a window where the incident electromagnetic radiation R can pass through the second membrane 22 to the measuring element 18, as explained above. Also in this embodiment the membranes and layers described are provided by thin film deposition.

For example, the first membrane 16 and/or the second membrane 22, in particular its layer(s), can be made of silicone dioxide and/or silicon nitride. For example, the measuring element (or thermistor) 18 can be made of vanadium oxide. For example, the first sacrificial layer 14 and/or the second sacrificial layer 20 can be made of aluminium or an aluminium alloy (e.g. an aluminium-copper alloy) or polysilicon. The manufacturing method or process can for example have a maximum temperature below 400° C. In this way the method or process is compatible with an ASIC on which the substrate is arranged. For example, the first membrane 16 and/or the second membrane 22 or its layers (e.g. made of silicone dioxide and/or silicon nitride) can be provided or applied using plasma-enhanced chemical vapor deposition (PECVD).

As mentioned above, the first cavity 24 and/or the second cavity 26, in particular of the bolometer of the first embodiment (see FIG. 1) or the bolometer of the second embodiment (see FIG. 3), comprise a gas having a pressure lower than the atmospheric pressure (e.g. vacuum). The gas can for example be (low-pressure) gas remainders that are accumulated in the first and/or second cavity during manufacturing, in particular during sealing with the seal or plug 23. For example, the gas can comprise at least one of $SiH_4$, $NH_3$, $N_2$, and reaction products. For example, the pressure of the gas can be between 0.5 and 5 Torr, in particular between 2 and 3 Torr, or vacuum. However, it will be understood that the gas can have any other suitable pressure (lower than the atmospheric pressure) and/or can be any other suitable gas or gas mixture.

As mentioned above, the bolometer of the first embodiment of FIG. 1 or the bolometer of the second embodiment of FIG. 3 has a first membrane 16 comprising a single measuring element 18. By using a single measuring element 18 enclosed or covered by the second membrane 22, thermal coupling between two or multiple measuring elements can be prevented, in particular when using multiple bolometers in a thermal imaging sensor. Further, compared to a solution where multiple measuring elements are enclosed or covered by one single membrane, the total diameter of the bolometer (and the total diameter of the second membrane 22) is smaller and thus the thickness of the enclosing (or covering) second membrane 22 can be thinner, while still withstanding ambient air pressure (about 1 Bar). As the collapse pressure (the pressure that is needed to collapse a membrane) scales as membrane thickness^3/membrane radius^4, a membrane having a larger diameter would need to be thick, which would be bad for the absorption of light.

Figure 5:
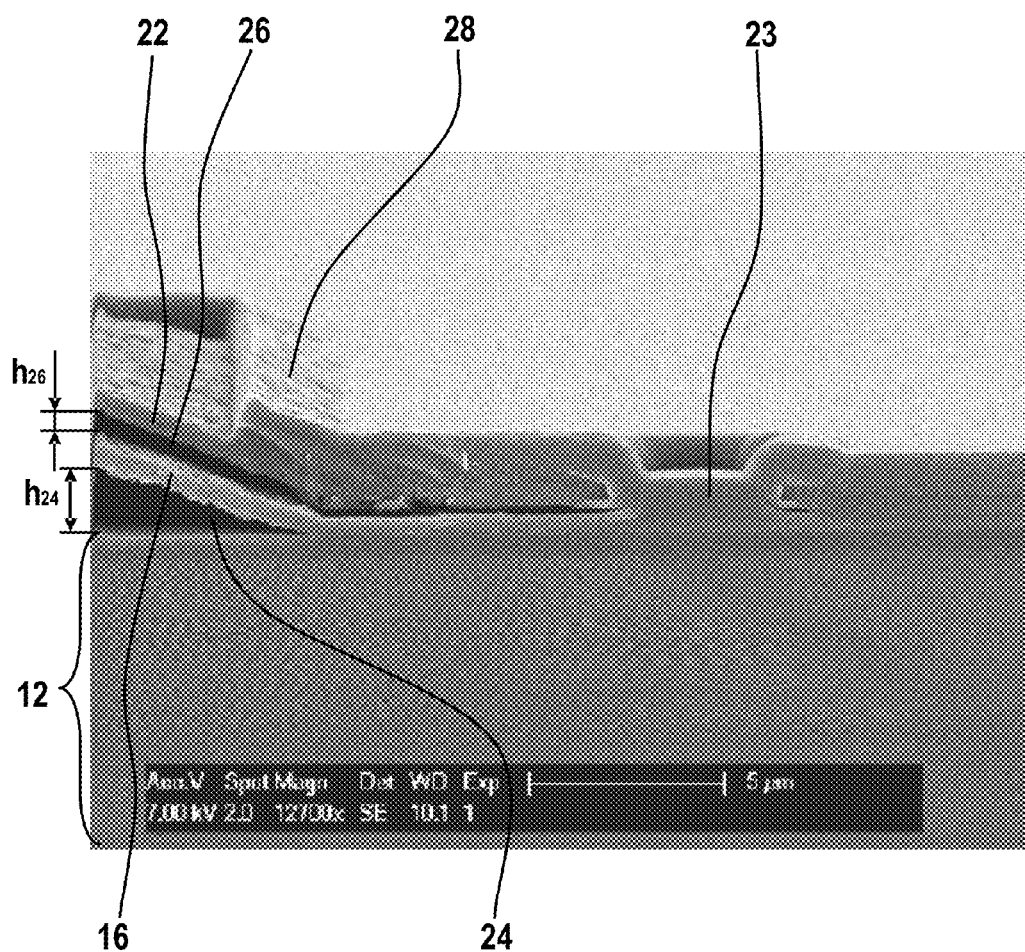
FIG. 5 shows a first image of a cross-section of an exemplary bolometer according to the second embodiment.
Figure 6:
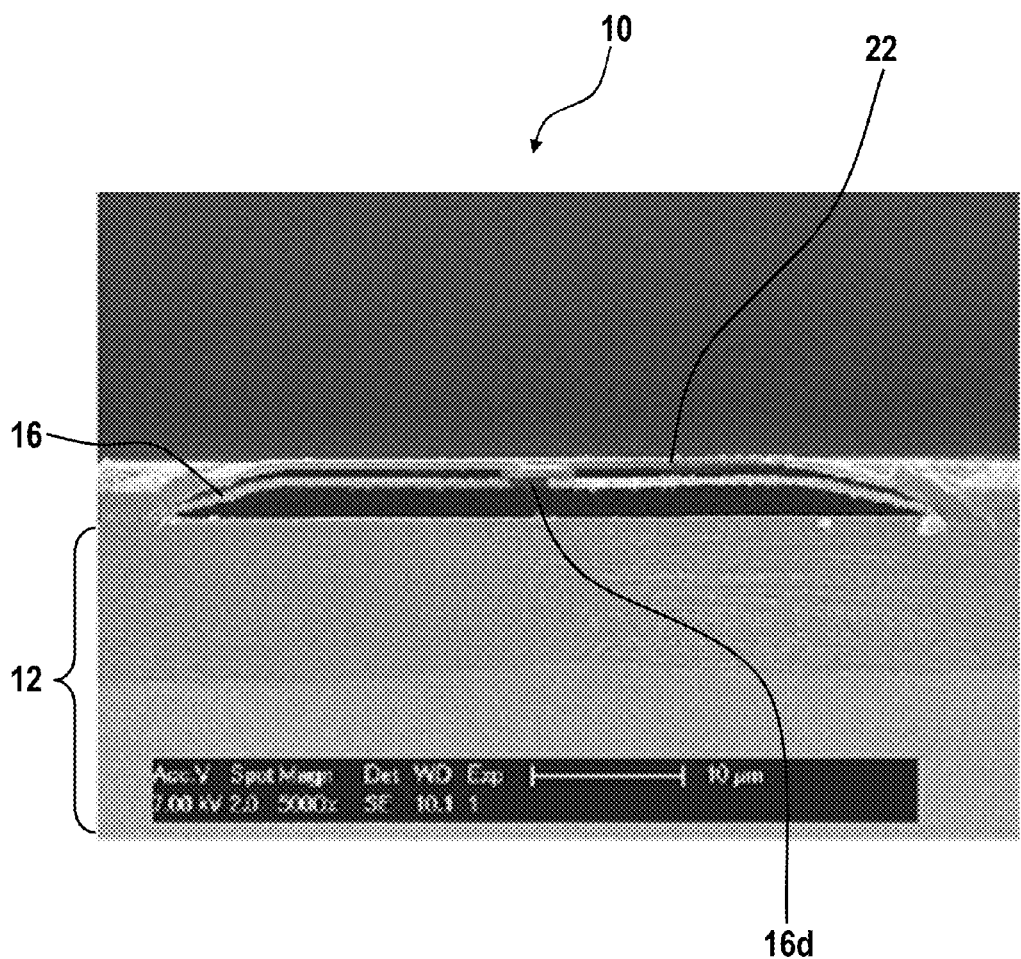
FIG. 6 shows a second image of the cross-section of the exemplary bolometer according to the second embodiment.

FIG. 5 shows a first image of a cross-section of an exemplary bolometer according to the second embodiment, as explained with reference to FIG. 3 and FIG. 4. In FIG. 5 in particular the seal or plug 23 sealing the etch hole 22d can be seen. FIG. 6 shows a second image of the cross-section of the exemplary bolometer (FIG. 5) according to the second embodiment, as explained with reference to FIG. 3 and FIG. 4. In FIG. 6 in particular the hole 16d in the first membrane 16 can be seen through which the etching agent, introduced through the etch hole 22d, reaches to the first sacrificial layer 14. In FIG. 5 and FIG. 6 the second membrane 22 has a thickness of about 0.5 μm. The first cavity 24 has a height $h_{24}$ of about 2.5 μm which is bigger than a height $h_{26}$ of the second cavity 26 of about 0.5 μm. The total diameter of the bolometer is about 50 μm. However, it will be understood that the dimensions of FIG. 5 and FIG. 6 are exemplary and that the bolometer can be manufactured in any other suitable dimensions.

Figure 7:
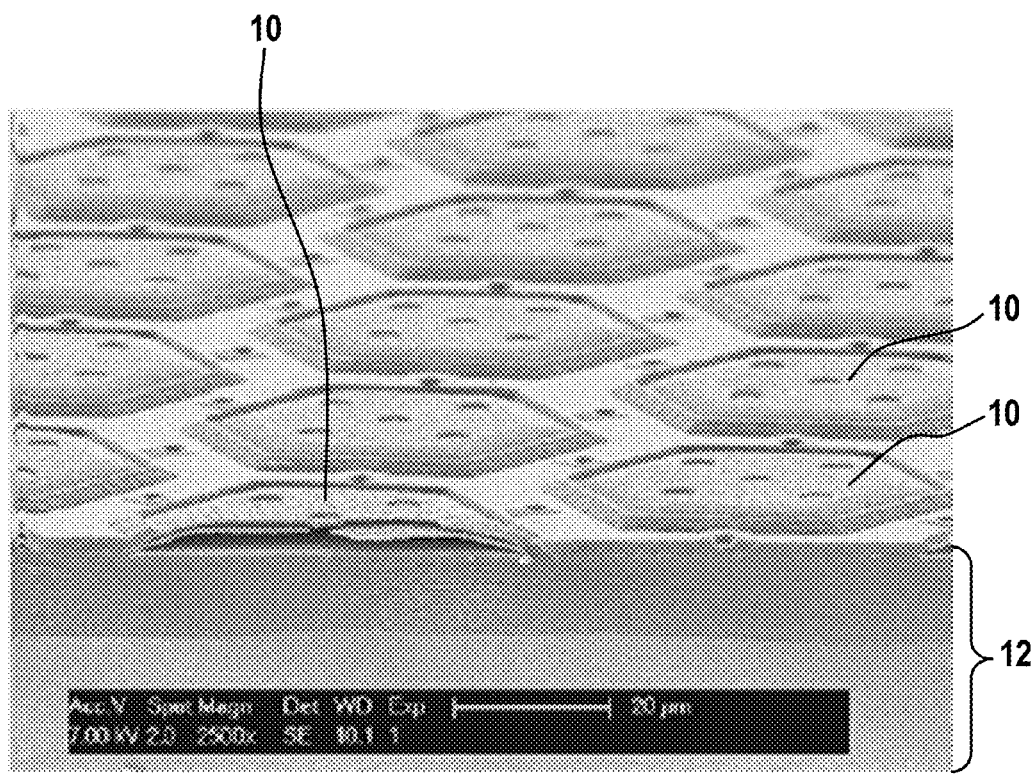
FIG. 7 shows an image of an exemplary thermographic image sensor comprising a plurality of bolometers according to the second embodiment.

FIG. 7 shows an image of an exemplary thermographic image sensor comprising a plurality of bolometers 10 according to the second embodiment, as explained with reference to FIG. 2 to FIG. 6. A thermographic image sensor comprising a plurality of bolometers 10 is used for providing a thermographic image of an object irradiating electromagnetic radiation in form of infrared light. The plurality of bolometers 10 are arranged in an array on a common substrate 12. Each of the bolometers 10 measures an amount of incident electromagnetic radiation using the measuring element or thermistor. An electrical circuit (not shown) connected to the measuring element or thermistor senses a resistance change of the thermistor in order to detect a temperature change. From theses detected temperature changes or data of the plurality of bolometers 10 the thermographic image can be reconstructed. The thermographic image sensor can further comprise a dedicated ASIC for temperature data collection and signal processing. Further, the thermographic image sensor can include wiring to an external unit for signal processing and/or for displaying of the thermographic image. Optionally, the thermographic image sensor can have an additional optical lens (e.g. made of Germanium and/or Silicon). Also optionally, the thermographic image sensor can have an arrangement for cleaning the surface for second membrane) of the bolometer, for example by means of a fluid (e.g. water) or a gas (e.g. air) flow.

The thermographic image sensor can then be used in multiple ways. For example, a medical device (e.g. endoscope or catheter) can comprise such thermographic image sensor. Such a medical device can for example be used in minimal invasive procedures, e.g. of the lungs. For example, the thermographic image sensor can be located on the medical device so as to have a 360° view.

The bolometer 10 can have a hexagonal shape, as for example shown in FIG. 7 (when viewed from the top). Bolometers having a hexagonal shape can in particular be efficiently packed in an array. Thus, bolometers having a hexagonal shape packed in an array yield a high fill factor. However, it will be understood that the bolometer(s) described herein can have any other suitable shape, for example a round shape or square shape. For example, a bolometer having a round, in particular circular, shape has a gradual stress distribution.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A bolometer comprising: a substrate, a first membrane formed by removing a first sacrificial layer on the substrate, the first membrane comprising a measuring element for measuring an amount of incident electromagnetic radiation, a second membrane formed by removing a second sacrificial layer on the first membrane, the second membrane enclosing the first membrane, a first cavity formed between the substrate and the first membrane, and a second cavity formed between the first membrane and the second membrane.

2. The bolometer of claim 1, the first membrane comprising two end portions where the first membrane is attached to a planar surface of the substrate and a middle portion arranged on the first sacrificial layer such that the middle portion of the first membrane is spaced apart from the planar surface of the substrate when the first sacrificial layer is removed.

3. The bolometer of claim 1, the second membrane comprising two end portions where the second membrane is attached to the first membrane and a middle portion arranged on the second sacrificial layer such that the middle portion of the second membrane is spaced apart from the first membrane when the second sacrificial layer is removed.

4. The bolometer of claim 1, wherein the incident electromagnetic radiation is infrared light.

5. The bolometer of claim 4, wherein the second membrane has a thickness which is selected such that the infrared light can pass through the second membrane to the measuring element.

6. The bolometer of claim 1, further comprising a cover layer on the second membrane, and comprising a hole in the cover layer to provide a window where the incident electromagnetic radiation can pass through the second membrane to the measuring element.

7. The bolometer of claim 1, wherein the second membrane has a thickness between 0.3 μm and 0.8 μm, in particular between 0.4 μm and 0.6 μm.

8. The bolometer of claim 1, wherein the first membrane comprises a single measuring element.

9. The bolometer of claim 1, wherein the substrate comprises a mirror layer comprising a reflective mirror for reflecting the incident electromagnetic radiation.

10. The bolometer of claim 1, wherein the first sacrificial layer and the second sacrificial layer are removed in a common etching step.

11. The bolometer of claim 1, the first cavity and/or the second cavity comprising a gas having a pressure lower than the atmospheric pressure.

12. The bolometer of claim 1, wherein the measuring element is a thermistor.

13. The bolometer of claim 1, wherein the membranes and layers are provided by thin film deposition.

14. A thermographic image sensor for providing a thermographic image of an object irradiating electromagnetic radiation in form of infrared light, the thermographic image sensor comprising a plurality of bolometers according to claim 1 which are arranged in an array on a common substrate.

15. A method of manufacturing a bolometer, the method comprising the steps of: providing a first sacrificial layer on a substrate, providing a first membrane on the first sacrificial layer, the first membrane comprising a measuring element for measuring an amount of absorbed incident electromagnetic radiation, providing a second sacrificial layer on the first membrane, providing a second membrane on the second sacrificial layer such that the second membrane encloses the first membrane, removing the first sacrificial layer such that a first cavity is formed between the substrate and the first membrane, and removing the second sacrificial layer such that a second cavity is formed between the first membrane and the second membrane.

\* \* \* \* \*